United States Patent [19]
Lung et al.

[11] Patent Number: 5,357,786
[45] Date of Patent: Oct. 25, 1994

[54] DEVICE FOR DETERMINING MECHANICAL PROPERTIES OF MATERIALS

[75] Inventors: Charles A. Lung; On K. Chang, both of San Jose, Calif.

[73] Assignee: Valence Technology, Inc., San Jose, Calif.

[21] Appl. No.: 101,871

[22] Filed: Aug. 4, 1993

[51] Int. Cl.$^5$ .............................................. G01N 3/48
[52] U.S. Cl. ................................................ 73/81
[58] Field of Search ............................. 73/81, 82, 85

[56] References Cited

U.S. PATENT DOCUMENTS

| | | | |
|---|---|---|---|
| 908,623 | 1/1909 | Stillman | 73/81 |
| 2,544,205 | 3/1951 | Williams | 73/81 |
| 2,638,779 | 5/1953 | Wilson | 73/81 |
| 2,699,540 | 1/1955 | Hunter | 73/81 |
| 4,820,051 | 4/1989 | Yanagisawa et al. | 73/81 |

FOREIGN PATENT DOCUMENTS 280292 11/1927 United Kingdom ................ 73/81

*Primary Examiner*—Robert Raevis
*Attorney, Agent, or Firm*—Linda M. Deschere

[57] ABSTRACT

There is provided a method for measuring and evaluating hardness or toughness of relatively delicate materials such as polymers, semi-solids, colloids or gels to determine the firmness thereof by inserting a stylus a specific depth into the material and then determining how the material itself reacts by measuring a resultant opposing force caused by insertion of the stylus. The device used in the method of the invention comprises a stylus (plunger) to vertically impinge on the sample when the stylus is displaced vertically downward. An actuating means controls downward movement of the stylus. The actuating means comprises a movable shaft and a stationary sleeve. The shaft has one end which is threaded and a second end which is constructed and arranged to carry the stylus. The stationary sleeve has internal threads for cooperative engagement with the external threads of the shaft, whereby adjustment by the threads causes vertical movement of the stylus.

18 Claims, 3 Drawing Sheets

DEVICE FOR DETERMINING MECHANICAL PROPERTIES OF MATERIALS

FIELD OF THE INVENTION

This invention relates to a new and improved testing device for determining the hardness or firmness of a very thin film or layer of coating, usually of a polymeric, semi-solid, colloid or gel material, and further relates to a new and improved method of testing such hardness or firmness.

BACKGROUND OF THE INVENTION

The hardness of plastic materials is typically determined by use of a durometer. A durometer is used for measuring hardness of plastic material such as polyethylene, polypropylene, polyurethane, thermoplastic elastomer tubing and natural rubber. The durometer measures the amount of reflected bounce of a special hammer of the material being tested. Generally, the harder the material, the greater will be the rebound. Plastic tubing, for example, is tested using a durometer in what is known as a Shore A test. A Rockwell hardness test is commonly used to test plastic materials for resistance to indentation. In the test, a diamond or steel ball, under pressure, is used to pierce the test specimen. A 10-kilogram weight is first applied and the degree of penetration noted. The so-called major load (60 to 150 kilograms) is next applied and a second reading obtained. The hardness is then calculated as the difference between the readings and expressed with nine different prefix letters to denote the type of penetrator used and the weight applied as the major load.

Other methods for testing hardness rely on pressing an indenter into a flat sample by means of a load applied to the indenter. After removing the indenter and applied load, an impression is left as a result of deformation and an optical measurement of the width of the impression provides data from which hardness is calculated. For example, U.S. Pat. No. 4,699,000 describes a method for testing the hardness of metals by continuously recording both the applied load and the displacement of the indenter for determining metal characteristics such as modulus, yield stress, impact, hardness or strength, creep, and fatigue. As in the case of the conventional durometer, the method of the 4,699,000 patent is not usable for determining toughness or hardness of delicate or semi-solid materials.

The foregoing techniques are simply not useful for measuring the toughness, firmness or hardness for materials which are extremely delicate or fragile and which are in the form of a thin film or thin layer of coating. For such delicate materials, conventional devices and methods would destroy the sample without revealing anything about its hardness or toughness.

Therefore, what is needed is a new device and method for testing the mechanical properties of delicate polymeric, semi-solid, colloid or gel material in the form of a film or a layer of coating with a thickness of as little as 10 microns.

BRIEF SUMMARY OF THE INVENTION

In order to measure the depth of penetration of the stylus into a sample, measuring means consisting of points (divisions) at regular intervals along the external surface of a sleeve are provided which cooperate with a thimble fitted over the sleeve and fixed to the threaded end of a shaft. The thimble being fixed to the shaft, moves with the shaft along the sleeve as the shaft is displaced vertically. Thus, the thimble moves along the sleeve and along the divisions marked at regular intervals. The shaft, sleeve and thimble are essentially in the form of a super-fine micrometer with the thimble having the sensitivity of, preferably, two microns per division. Preferably, a diamond stylus is carried at an end of the shaft opposite the thimble. This micrometer has the capacity to move the diamond stylus an exact distance into the sample and it is capable of controlling the motion to within the stated two microns.

The sample into which the stylus is inserted rests upon a support. The support has means for measuring force due to the downward displacement of the stylus such that when the stylus impinges a predetermined distance downward from an upper major surface of the sample, the support responds to the force imposed by such movement. Typically the stylus is inserted nominally 20 to 25 microns into the sample and the resultant force is measured on an analytical balance to a sensitivity of 0.1 mg (milligrams). Thus, the force measuring means, being an analytical balance, produces an output reading typically in milligrams which is correlatable to the degree of firmness or the degree of cure of the material of the sample. The force registered by the analytical balance is related to the toughness, firmness or hardness of the sample.

Accordingly, it is an object of the invention to provide a device and method which are relatively easy and simple to use and are highly suited for measuring relative hardness, firmness or degree of cure of, particularly, semi-solid, colloidal, or gel materials which would not be capable of being measured and which would be essentially uncharacterizable by conventional means.

These and other objects, features and advantages will become apparent from the following description of the preferred embodiments, appended claims and accompanying drawings.

DETAILED DESCRIPTION OF THE PREFERRED EMBODIMENTS

Force Application and Control

Figure 1:
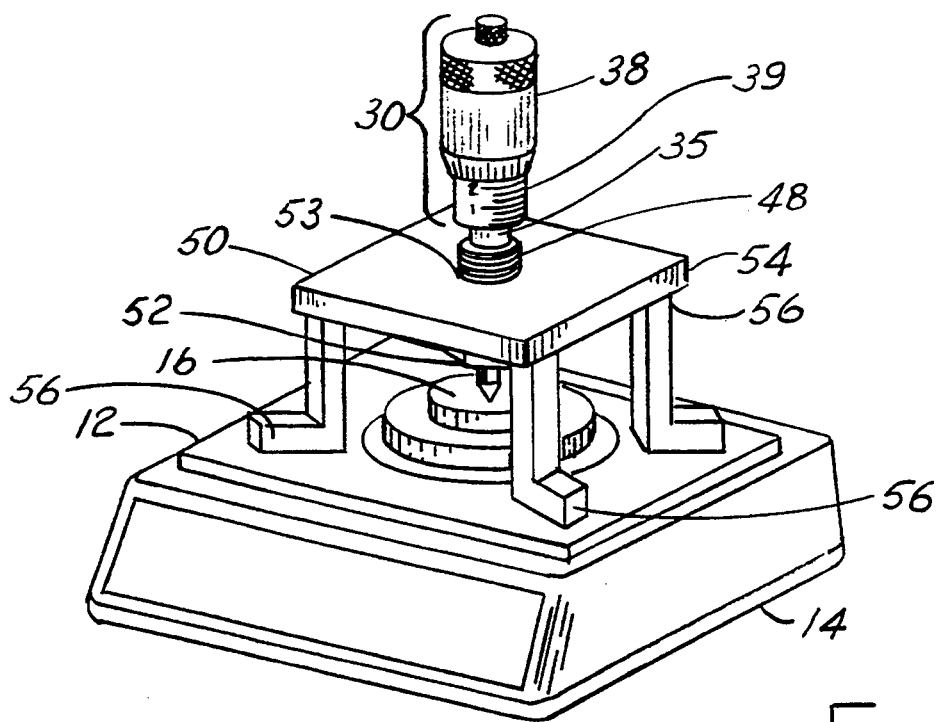
FIG. 1 is a perspective view of a device for testing material hardness or firmness in accordance with the present invention.
Figure 2:
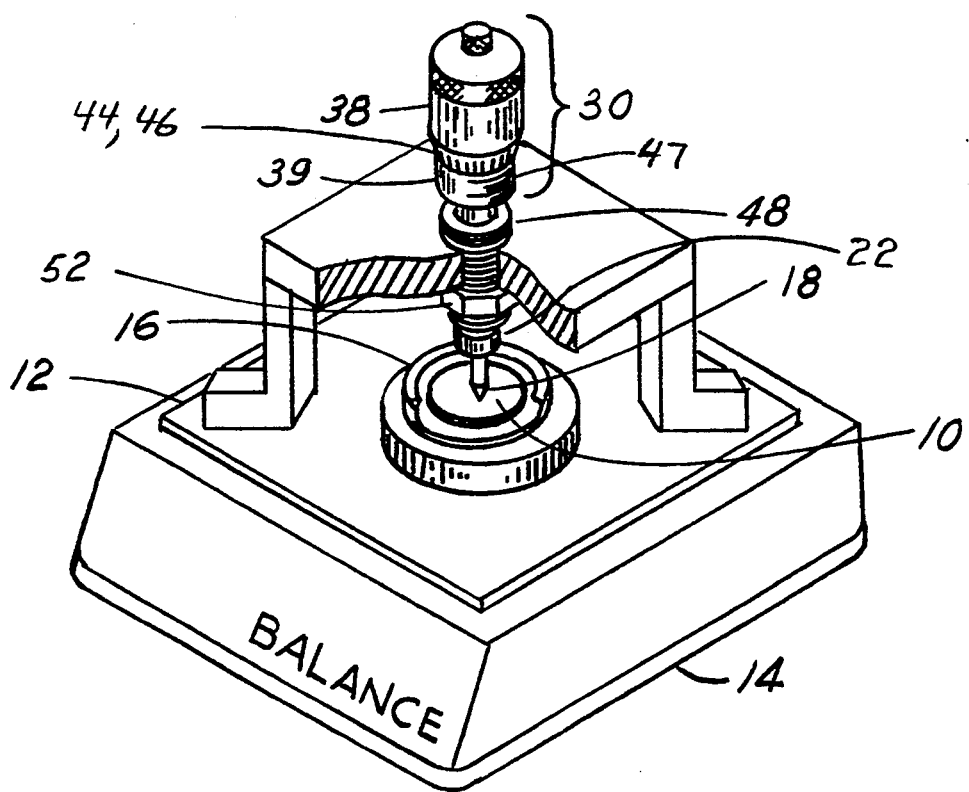
FIG. 2 is a perspective view, partially in section, of the device in FIG. 1 shown with a test sample positioned on the device.
Figure 3:
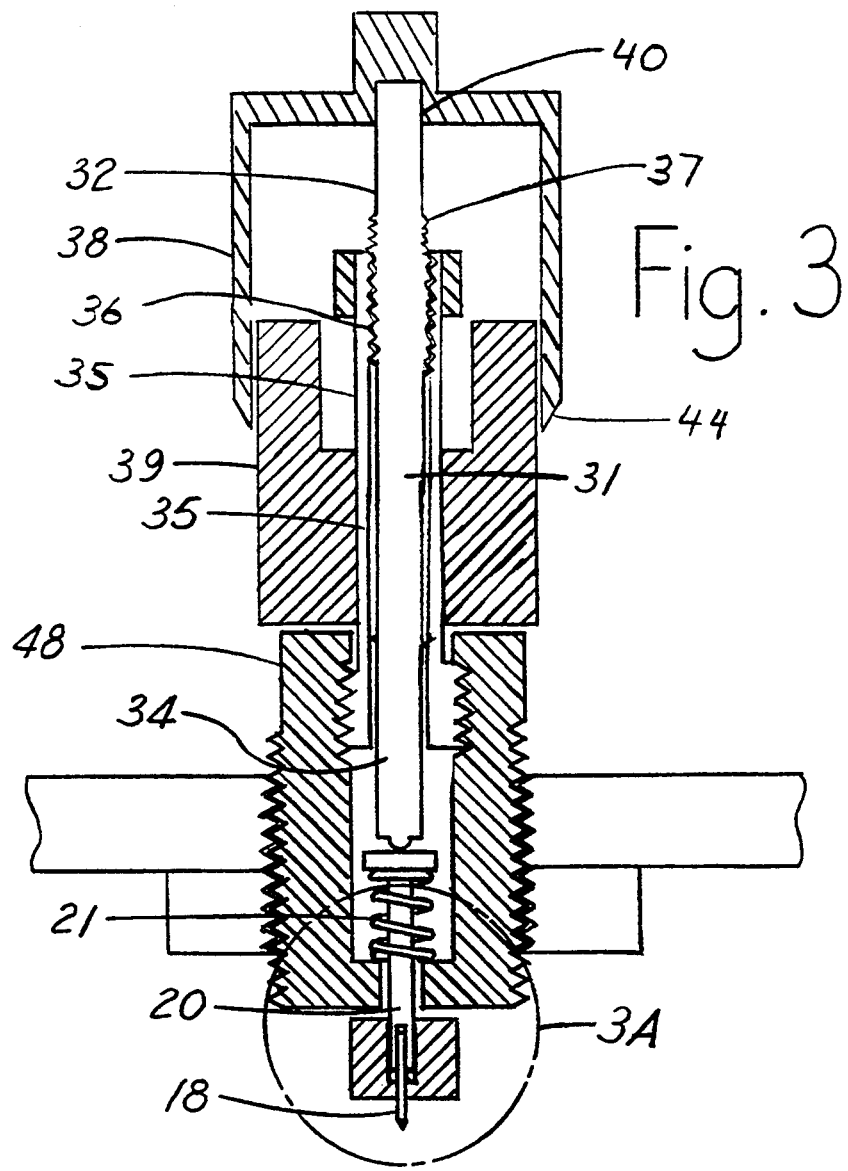
FIG. 3 is a partial sectional view of the shaft and actuator of the device in FIGS. 1 and 2.
Figure 3A:
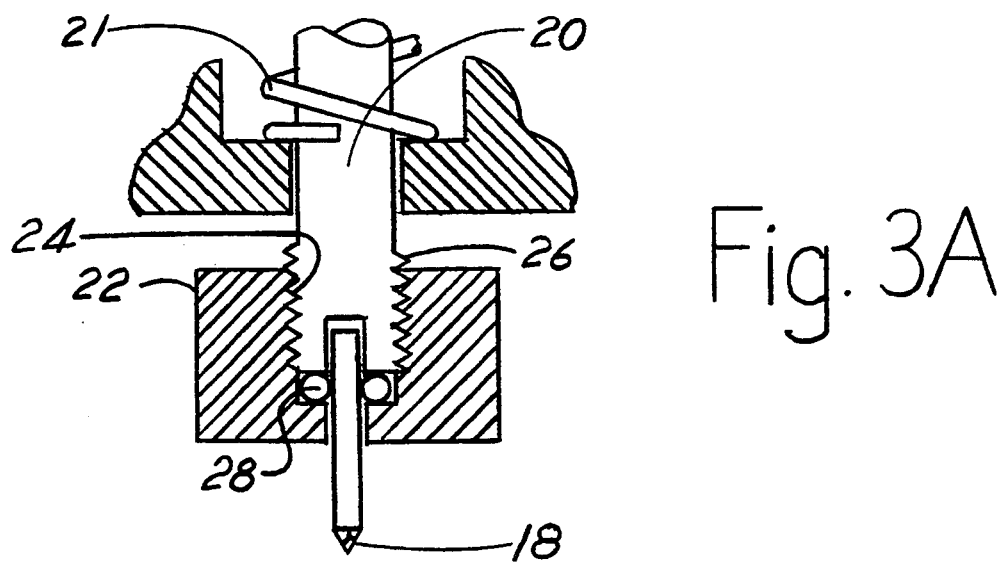
FIG. 3A is an enlarged view of the encircled portion of FIG. 3.

FIGS. 1 and 2 show one embodiment of the present invention in which a sample 10 to be tested is placed on a support 12 which comprises force measuring means 14. The sample 10 is retained by a holder 16 on the support 12 below a plunger or stylus 18 (FIGS. 3 and 3A). The stylus 18 is carried by a push rod 20 which is maintained in a retracted position by a spring 21. Stylus 18 is retained in push rod 20 by nut 22 which has internal threads 24 to engage external threads 26 of rod 20. O ring 28 is optionally included in the assembly. The rod 20 is moved by actuating means 30 which includes steel rod 31. Rod 31 has first and second ends 32, 34 which preferably form a portion of actuating means 30 for controlling upward and downward movement (displacement) of the stylus 18. The actuating means 30 comprises movable steel rod 31 in a stationary steel sleeve or tube 35. FIG. 3 shows actuating means 30 partially in cross-section. The steel rod 31 has a first end 32 which is disposed in the steel sleeve 35 and a second end 34 constructed and arranged to carry the stylus 18. The stationary sleeve 35 has internal threads 36 which engage threads 37 of steel rod 31 whereby rotation of steel rod 31 causes vertical movement of the stylus 18 carried by push rod 20.

The actuating means 30 also indicates vertical movement of the stylus 18 as the actuating means 30 is in the form of, or similar to, a micrometer gauge. Actuating means 30 has an upper body or thimble 38 and a lower body 39. The axis of the steel tube or sleeve 35 and rod 31 are at right angles to the major surface of the sample 10 in holder 16 and to the top surface of the support 12. The threads 37 of the steel rod 31 are in the form of a measuring screw of fine pitch to fit the internal threads 36 of sleeve 35. More specifically, affixed to the outer end 40 of the steel rod 31 (screw) is the thimble 38 fitting over the lower body 39 (nut). The edge 44 of the thimble 38 is beveled so that equally, circumferentially spaced graduations 46 placed on the edge 44 come very close to the lower body 39. Equally axially spaced, circumferentially extending reference lines 47 on the lower body 39 lie in planes perpendicular to its axis and provide a graduated scale indicating the pitch of the threads of steel rod 31 (screw). The beveled edge 44 of the thimble 38 is marked with dividing or graduating lines 46 so that rotating the thimble from one reference line 47 to the next on the lower body 39 indicates a vertical movement of the measuring point, that is, point of the stylus 18. For example, if the pitch of a measuring screw is one millimeter (1 mm), there should be 100 divisions on the thimble 38, then by rotating the thimble 38 one division, the stylus 18 will be advanced 0.010 mm. In order to achieve a super fine resolution of the micrometer of two microns (0.002 mm), it is preferred that the threaded end 32 of rod 31 (measuring screw) of the invention should have a pitch of 0.500 mm, and the thimble 38 should have 250 divisions. Thus, the preferred actuating means 30 of the invention is capable of controlling the motion to within two microns as the stylus 18 is inserted into the surface of the sample to be analyzed. Therefore, the actuating means 30 of the invention includes measuring means consisting of the thimble 38 having the circular scale of circumferentially spaced points 46 thereon where the thimble 38 extends over and is fixed to the first end 32 of the rod 31 and the scale defined by axially spaced apart lines 47 on the lower body 39 cooperate with thimble 38 to indicate vertical displacement of the rod 31 as the rod 31 and thimble 38 move relative to the stationary sleeve 35 and the stationary lower body 39.

The following is a brief explanation of how the actuating means or micrometer-type device 30 is used in the invention: Referring to the drawing, it can be seen that the stylus 18 is not directly attached to the micrometer 30. The stylus 18 is attached to the end of the push rod 20. The push rod 20 fits inside adapter 48 snugly and is free to slide vertically. The adapter 48 is threaded into the frame 50 and is secured with a lock nut 52 under an opening 53 of the frame. The micrometer 30 is threaded into the top of the adapter 48. The steel rod 31 of the micrometer 30 pushes against the top of the push rod 20, which is spring loaded. When the thimble 38 of the micrometer 30 is turned, the steel rod 31 of the micrometer 30 moves vertically. The push rod 20 transmits the movement to the stylus 18. Accordingly, the actuating means 30 is supported above the sample holder 16 of support 12 by adapter 48 in frame 50. The adapter 48 is fitted into an opening 53 in the top plate 54 of frame 50. Legs 56 of the frame 50 support the plate 54 above the sample holder 16. The stationary adapter 48 carries sleeve 35 in opening 53 above sample 10 so that stylus 18 is initially spaced from the sample 10.

Figure 4:
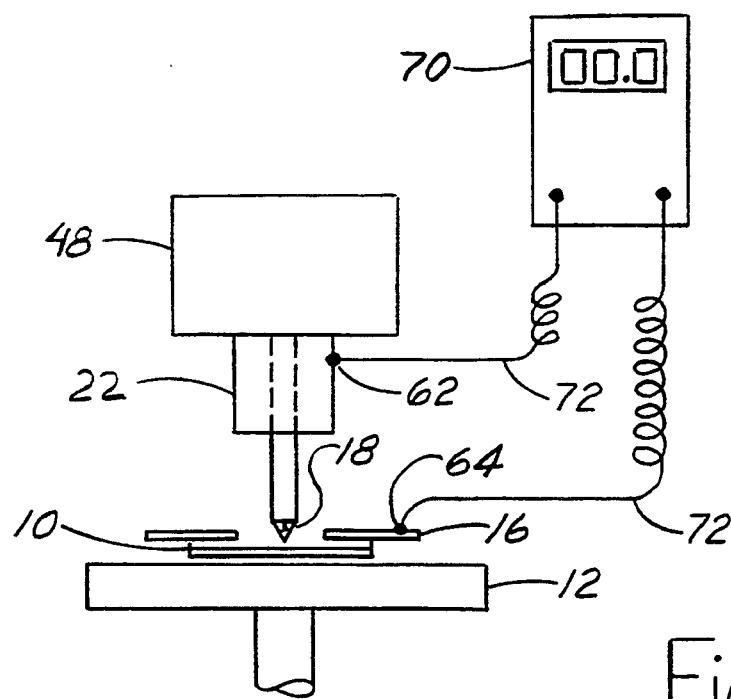
FIG. 4 is a frontal schematic view of a portion of the device in FIGS. 1 and 2 shown with the electrical apparatus for detecting when the stylus first contacts the sample.

As shown in FIG. 4, initial contact between the stylus 18 and the major surface of the sample 10 is detected. This is accomplished by an electrical method since samples of interest exhibit at least a detectable conductivity. A portion of the micrometer assembly 30 is one connector terminal 62 and is in electrical contact with a diamond stylus 18 by gold coating the diamond stylus 18. The other connecter 64 of this electrical couple is the table or support 12 with the sample 10 and the sample holder 16. The (table) support 12 carries the steel sample hold down holder 16 and is electrically conductive. The first contact is sensed by using a voltmeter 70 and measuring resistance in ohms through leads 72. The meter 70 will indicate a resistance as soon as the gold-coated stylus 18 contacts the top of the sample surface (i.e. a reading of an open circuit changes to a small resistance). This is the point at which the "hardness" measurement is begun and from which the predetermined penetration depth of 20 to 25 microns is made.

Force Measuring

The support 12 for holding the sample 10 includes force measuring means 14 which may be of a variety of designs by which an unknown force may be measured including the following: 1) balancing against the known gravitational force on a standard mass, either directly or through a system of levers; 2) measuring the acceleration of a body of known mass to which the unknown forces apply; 3) electromagnetic force compensation by balancing against a magnetic force developed by interaction of a current-carrying coil and a magnet; 4) transducing the force to a fluid pressure and then measuring the pressure; 5) applying the force to some elastic member (i.e. spring) and measuring the resulting deflection; 6) measuring the change in precession of a gyroscope caused by an applied torque related to the measuring force and; 7) measuring the change in natural frequency of a wire tensioned by the force.

It is preferred that an electromagnetic balance be used rather than the more conventional analytical balance or platform balance. Conventional balances will be described first, then the preferred electromagnetic balance. In a typical analytical balance, the beam is designed so that the center of the mass is only slightly below the knife edge point and, thus, barely in stable equilibrium. This makes the beam deflection, particularly in sensitive instruments read with an optical micrometer, a very sensitive indicator of unbalance. Often the beam deflection is used as the output reading rather than attempting to null by adding mass or adjusting arm length of a poise weight. This approach is faster than nulling but requires that the deflection angle unbalanced relation be accurately known and stable. For highly accurate measurements, the buoyant force due to the immersion of the standard mass in air must be taken into account. For particularly sensitive measurements, the balances must be installed in temperature controlled chambers and manipulated remotely to reduce the effects of the operator's body and conduction currents.

Commercially available analytical balances may be classified as follows: macro analytical with a range of 200 to 1000 grams and a resolution of $10^{-4}$ grams; semi-micro analytical with a range of 50 to 100 grams and a resolution of $10^{-5}$ grams; and micro analytical for a range of 10 to 20 grams and a resolution of $10^{-6}$ grams. Micro and ultra-micro balances with respective ranges of less than one gram and less than 0.01 grams are also available. While analytical balances are usually used for weighing and while platform and pendulum scales are more typically employed for force measurements, all three instruments are useful for static-force measurements. A pendulum scale is a deflection-type instrument in which the unknown force is converted to a torque that is then balanced by the torque of a fixed standard mass arranged as a pendulum. The practical version of this principle utilizes specially shaped sectors and steel tapes to linearize the inherently non-linear torque angle relation of the pendulum. The unknown force may be applied directly or through a system of levers. An electrical signal proportional to force is easily obtained from any angular displacement transducer attached to measure the angle. The platform scale utilizes a system of levers to allow measurement of large forces in terms of much smaller standard weights. The beam is brought to null by a proper combination of pan weights and adjustment of the poise weight lever arm along its calibrated scale. The scale can be made self-balancing by adding an electrical displacement pick-up for null detection and an amplified motor system to position the poise weight to achieve null. This platform scale may be arranged so that the reading is essentially independent of the location of the force on the platform.

Other types of force measuring systems include the preferred electromagnetic balance which utilizes a photoelectric or other displacement sensor, null detector and amplifier in a torquing coil in a servo system to balance differences between the unknown force and the gravity force on a standard mass. Hydraulic or pneumatic cells may also be used in which the application of a load or force increases fluid pressure which is then read on an accurate gauge. Electrical pressure transducers can be used to obtain an electrical signal readout. Pneumatic cells use a nozzle-flapper transducer as a high gain amplifier in a servo loop. Application of a force causes a diaphragm deflection which in turn causes a pressure increase acting on the diaphragm with an effective counterforce causing the system to come to equilibrium at a corresponding pressure indicative of the force. Elastic deflection transducers are widely used for both static and dynamic loads of frequency content up to many thousands hertz. While all are essentially spring mass systems with intentional or unintentional damping, they differ mainly in the geometric form of "spring" employed and in the displacement transducer used to obtain an electrical signal. The displacement sensed may be gross motion or strain gauges. The displacement transducer range to measure motion in the sensitive direction will measure only that component of applied vector force which lies along the sensitive axis which is therefore applicable to the practice of the present invention.

The preferred electronic balance utilizing electromagnetic force compensation will now be described. In the evolution of electronic (more accurately, electromechanical) balances, one operating principle, electromagnetic force compensation, emerged early as the standard in high-precision weighing. In every electromechanical weighing system, there are three basic functions. (1) The load-transfer mechanism, composed of the weighing platform or pan, levers, and guides, receives the weighing load on the pan as a randomly distributed pressure force (P) and translates it into a measurable single force (F). (2) The electromechanical force transducer converts the mechanical input force into an electrical output, for example, voltage, current, or frequency. (3) The electronic signal-processing part of the balance receives the output signal, converts it to numbers, performs computation, and displays data.

In electronic balances load-transfer mechanisms are lever linkages similar to those used in mechanical substitution balances. As a refinement, the traditional knife-edge pivots have been replaced by elastic flexure pivots.

In a laboratory balance the transducer in many cases resembles the configuration of an electrodynamic loudspeaker. A sound-modulated current in the speaker coil interacts with the magnetic field in the circular gap of the permanent magnet, generating an oscillating force on the coil and voice cone assembly and thus producing sound waves.

Figure 5:
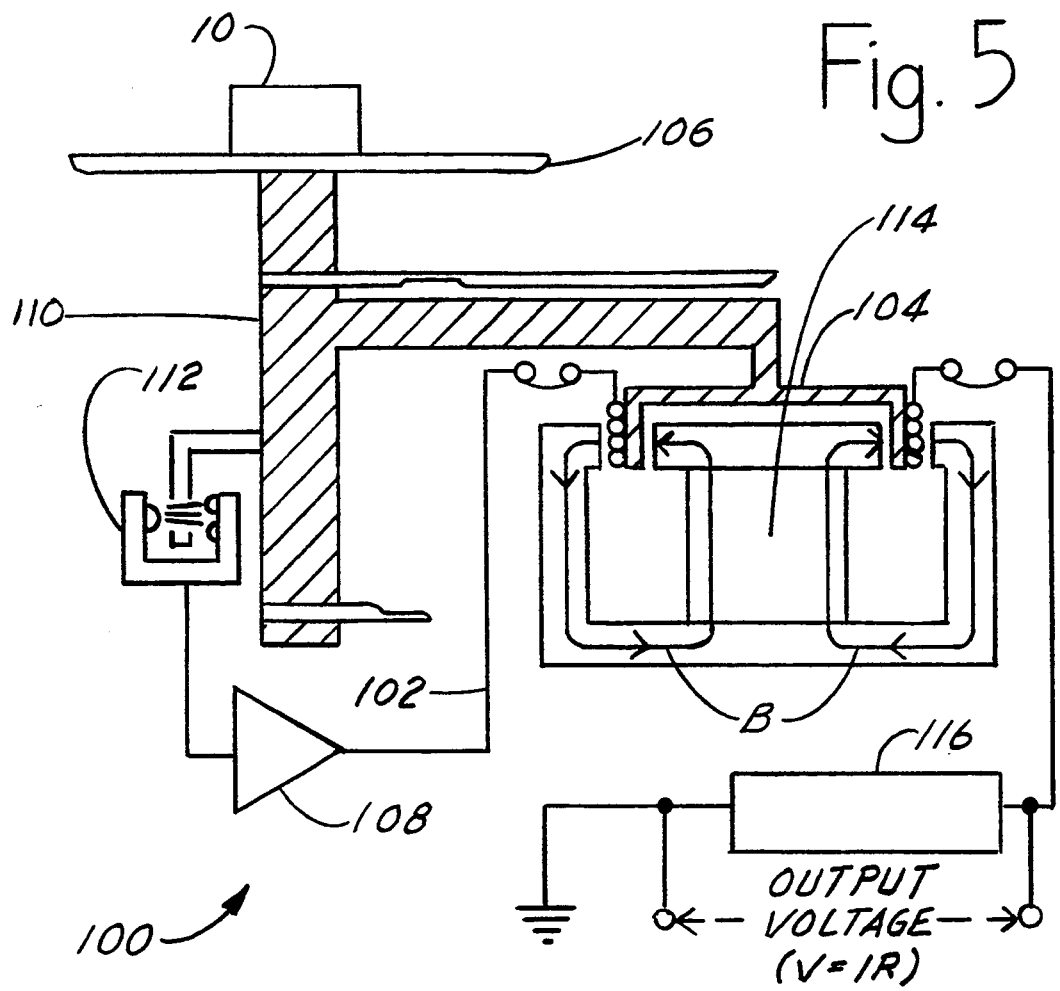
FIG. 5 is a diagrammatic schematic of a system incorporating the electromagnetic force compensation principle where output voltage is proportionate to the weight on the pan.

In the electromagnetic force compensator 100 (FIG. 5), a unidirectional current 102 generates a static force on the coil 104 which, in turn, counterbalances the weight force from the object 10 on the balance pan 106, usually aided by one or more force-reduction levers. The amount of coil current is controlled by a closed-loop servo circuit 108 which monitors the vertical deflections of the pan support 110 through a photosensor 112 and adjusts the coil current as required to maintain equilibrium between weighing load and compensation force.

The interactive force (F) between a magnetic field and a current-carrying conductor (at a right angle to each other) is determined by the equation below, $$F = IlB$$

whereby I represents the current, l is the total length of coil wire, and B is the magnetic flux density in the air gap. A cylindrical magnet 114 is a permanent magnetic core and soft iron jacket. The force F points in the third direction in space, that is, perpendicular to the directions of current and magnetic field. The force F, and with it the weight of the object on the balance pan, now results from a measure of the current I, for example, by measuring the output voltage V across a precision resistor 116 R wired in series to the force coil, and using the relationship $V = IR$.

The signal processing part of a balance can be thought of as a voltmeter whose dial face or digital indicator reads in units of weight. Therefore, the output voltage is proportionate to the weight on the pan. Signal processing in balances involves the most advanced methods of electrical measurement, as well as special computation routines that are applied to each weight value before it is displayed. There are five basic computations: (1) Tare subtraction; subtracts container weight or other preload from each weight value. (2) Automatic zero correction; compensates for tendencies of the measuring system to gradually wander off a set zero, even by a fraction of a display division. (3) Vibration filter; applies averaging or other noise-reduction techniques to measurement values in order to produce stable weighing results in the presence of building vibrations or other disturbances, for example in weighing live animals. (4) Stability detector; compares consecutive weighing results with each other, and blocks data output and signals a warning light when weighing results are transient or fluctuating. (5) Automatic calibration; as the operator presses a key and deposits a built-in or external mass standard on the balance, the instrument calibration factor is recalculated and stored in a nonvolatile (power-independent) memory.

EXAMPLE

The method of the invention was used to determine the hardness or toughness of a laminate comprising a polymeric, semi-solid material forming a portion of a lithium battery cell. The laminate consisted of an electrolyte and cathode components applied to an aluminum foil cathode current collector. The polymeric component was cured by electron beam radiation. After curing, the laminate remained soft. Depending on the degree of curing, the laminate may remain gel-like or become relatively more solid. More specifically, the laminate was layered as follows: 1) electrolyte composition of radiation cured polymers, (i.e. polyethylenically unsaturated liquid or non-liquid polymer precursors); 2) cathode composition of intercalation oxide compound, propylene carbonate, polyethylene oxide, and carbon particles; and 3) aluminum foil current collector. The thickness of the electrolyte, cathode and foil were, respectively, as follows: 40, 60 and 25 microns. Typical laminates had a total thickness of about 100 to 130 microns excluding the foil. The thickness of the electrolyte layer of interest was generally in the range of 25 to 60 microns. Typically, after curing, the cathode portion of the laminate is in the form of a somewhat cured paste and the electrolyte portion is relatively gel-like or semi-solid. The hardness of the laminate is thought to be nearly entirely dependant on the flowability or degree to which the electrolyte deforms or yields.

The device used in the method of the invention comprised an electromagnetic balance manufactured in Switzerland by Johnson Precisa, Model 125A, type 300-9213, serial #V97328. It was a typical electromagnetic balance with 125 gm capacity and sensitivity to 0.0001 gm. In the configuration of the example, the sample 10 was held by a tray which formed a part of the balance itself. Thus, the electromagnetic balance, including its tray, constituted the support 12 and force measuring means 14 as an essentially integral unit. The actuating means was a micrometer assembly 30 with a micrometer head from Newport Corporation, Fountain Valley, Calif. The unit is a Starrett thimble with 2.54 cm total travel and sensitivity is 0.002 millimeters per division (mm/div) or 2 microns per division. The stylus was a diamond cutting tool typically used in the electronics industry to trim hard disks. The tip of the stylus is tetragonal pyramidal with a dihedral angle of 90 degrees between two opposing faces. The stylus was clad with gold to provide an electrically conductive surface.

Electrical contacts were placed on the surface of the laminate and in contact with the gold-clad diamond tip. The electrical contacts made a circuit through a voltmeter to indicate when the top surface of the laminate made contact with the stylus tip. The test began by adjusting the micrometer to move the stylus downward until it just contacted the top surface of the laminate, as indicated by the resistance reading on the voltmeter. The balance was then zeroed out to a zero force reading. The micrometer was then used to advance the stylus about 20 microns downward so that the stylus entered the laminate to a depth of about 20 microns below the plane of initial contact. The resultant force was read on the balance and recorded. A series of tests were performed on each laminate sample, and typical readings of about 50 to 100 milligrams were obtained. Readings for a given sample were averaged and a standard deviation taken to represent the relative toughness, firmness, hardness or degree of cure.

Some tests were done using a layer of radiation cured electrolyte only, without the cathode paste layer. Readings on the balance of 32, 29.5, 27 and 30 milligrams where obtained. Another set of readings was taken on the entire laminate as described above, after curing. Results were 143 mg with deviation of 21, and 72.71 mg with deviation of 15 mg. The differences were due to the method by which the samples were prepared.

The method was also tested using conventional electrical tape. Test samples were prepared with one, two and three layers of tape respectively. Each layer of tape was 0.007 of an inch thick. In each case the stylus was inserted 10 microns into the sample. Respective readings were 59, 80, and 82 milligrams.

In some cases, the test was conducted while the stylus was left in its inserted position with force measurement readings taken in 30 second increments. A decay in the force was observed over time. The reduced force readings are thought to represent a decay in the pressure and the balance pan was actually moving up and approaching the stylus over time.

Although not wishing to be held to any particular theory, it is thought that the following applies. The hardness of a sample is in direct proportion to the weight registered on the balance. In the method of the invention, absolute values are not required. In the working examples given above, it was determined that a suitable quality of laminate was characterizable by a force on the order of 100 mg, with greater than 100 mg being most preferred. Thus, any reading approaching 100 or even greater, was acceptable when the stylus was inserted 20 to 25 microns into the sample. As a result, the method of the invention provided a very direct, simple, and useful quality control tool for screening manufactured laminate. The method and apparatus of the invention is also useful to test relative changes in mechanical properties such as hardness or toughness over a period of time, as in the case of a material which becomes harder with age. Therefore, the method and apparatus may be used in a variety of ways, yet the basic principle remains the same. That is, to determine how much the material will react to the insertion of the stylus, where such reaction is the resultant force as determined by force measuring means, preferably, an electromagnetic balance carrying the sample.

While this invention has been described in terms of certain embodiments thereof, it is not intended that it be limited to the above description, but rather only to the extent set forth in the following claims.

The embodiments of the invention in which an exclusive property of privilege is claimed are defined in the appended claims.

We claim:

1. A device for testing the firmness of a substantially flat sample having opposite first and second major surfaces, the sample containing a polymeric, semi-solid, colloid or gel material, comprising:
   a) a support having a planar surface and an electrically conductive portion on the planar surface for holding the sample on its first surface, the support comprising a balance having a deflection or displacement sensor responsive to application of force on the planar surface in a downward direction normal to the planar surface;
   b) a stylus to impinge on the second major surface of the sample when the stylus is displaced toward the sample;
   c) actuating means for controlling movement of the stylus, the actuating means comprising a movable shaft on which the stylus is mounted and a stationary sleeve positioned above the support and within which the shaft is disposed, the stationary sleeve and shaft being threadedly engaged whereby rotation of the shaft causes downward displacement of the stylus relative to the sleeve toward the sample; and
   d) means for detecting initial contact between the second surface of the sample and the stylus, the means comprising a first electrical contact which comprises the sample and the electrically conductive portion of the support, a second electrical contact on the stylus, and a meter between the contacts; whereby when the stylus just touches the second surface an electrical circuit is closed as indicated by the meter, and when the stylus penetrates a predetermined distance through the second major surface into the sample the support responds to the force imposed by such displacement as indicated by the balance, and the displacement and force are correlated to produce values related to the firmness, hardness, toughness or degree of cure of the material.

2. The device according to claim 1 wherein the actuating means comprises a stationary lower body and an upper body having a circular scale of circumferentially spaced points thereon, where the upper body is fitted over the lower body and fixed to the shaft, and a scale defined by axially spaced apart points on the lower body which cooperate with the upper body to indicate displacement of the shaft as the shaft and upper body move relative to the lower body.

3. A device for testing the firmness of a substantially flat sample having upper and lower major surfaces, the sample containing a polymeric, semi-solid, colloid, or gel material, comprising:
   a) a stylus to vertically impinge on the sample when the stylus is displaced vertically downward;
   b) actuating means for controlling downward movement of the stylus, the actuating means comprising a movable shaft and a stationary sleeve, the shaft having a first end which is threaded and a second end constructed and arranged to carry the stylus, the stationary sleeve having internal threads for cooperative engagement with the threaded shaft whereby adjustment by the thread causes vertical displacement of the stylus relative to the sleeve;
   c) a support having a planar support surface and a metallic portion on the planar surface for holding the sample;
   d means for detecting contact between the upper surfaces of the sample and the stylus, the means comprising a first electrical contact which comprises the sample and the metallic portion of the support, a second electrical contact on the stylus, and a voltmeter between the contacts such that when the stylus just touches the upper surface of the sample an electrical circuit is closed as indicated by the voltmeter; and
   e the support having a balance comprising an electromagnetic force compensation system with an output voltage proportionate to force exerted at the planar surface of the support for measuring force due to the downward displacement of the stylus such that when the stylus penetrates a predetermined distance downward from the upper major surface into the sample the support responds to the force imposed by such displacement as indicated by the balance, whereby the downward displacement and force are correlated to produce values related to the firmness, hardness, toughness or degree of cure of the material.

4. A method for determining the firmness of a substantially flat sample having opposite major surfaces, the sample containing a polymeric, semi-solid, colloid or gel material, comprising the steps of:
   a. providing a movable shaft having a stylus on one end to impinge on the sample when the stylus is displaced and actuating means for controlling movement of the shaft and stylus, the actuating means comprising the shaft being threadedly engaged with a stationary sleeve;
   b. supporting the sample on a planar surface of a support with one of the major surfaces of the sample opposing the stylus;
   c. rotating the threaded shaft to cause displacement of the stylus until initial contact is made between the tip of the stylus and the opposing major surface of the sample;
   d. detecting initial contact between the sample and the stylus by forming a first electrical contact which comprises the sample and an electrically conductive portion of the support, a second electrical contact on the stylus, and a meter between the contacts such that when the stylus just touches a surface of the sample an electrical circuit is closed as indicated by the meter;
   e. moving the stylus a preselected distance into the sample from the position of initial contact and causing a downward force on the sample and on the planar surface in a direction normal to the planar surface; and
   f. monitoring the force detected by a deflection or displacement sensor below the planar surface in response to the application of force on the sample and the planar surface.

5. The method according to claim 4 and further including comparing the monitored force and the preselected distance to known standards to assess the relative firmness of the sample.

6. The method according to claim 4 and including, before step (e), the step of calibrating the force measuring means to compensate for any force detected by the measuring means when such contact is made.

7. The method according to claim 4 wherein the stylus forms an integral part of the shaft.

8. The method according to claim 4 wherein the stylus is carried on one end of the shaft.

9. A method for determining the firmness of a substantially flat sample having upper and lower major surfaces, the sample containing a polymeric, semi-solid, colloid or gel material, comprising the steps of:
   a. providing a stylus to vertically impinge on the sample when the stylus is displaced vertically downward and actuating means for controlling downward movement of the stylus, the actuating means comprising a movable shaft and a stationary sleeve, the shaft having a first end which is threaded and a second end constructed and arranged to carry the stylus, the stationary sleeve having internal threads for cooperative engagement with the threaded shaft;
   b. placing a sample on a support comprising an upper planar surface and a metallic portion on the planar surface for holding the sample, and force measuring means below the planar surface comprising an electromagnetic force compensation system with an output voltage proportional to application of force at the planar surface;
   c. adjusting the threaded shaft to cause vertical displacement of the stylus until contact is made between the tip of the stylus and an upper major surface of the sample;
   d. detecting initial contact between the sample and the stylus by forming a first electrical contact which comprising the sample and the metallic portion of the support, a second electrical contact on the stylus, and a voltmeter between the contacts such that when the stylus just touches the upper surface of the sample an electrical circuit is closed as indicated by the voltmeter;
   e. moving the stylus a preselected distance downward into the sample from the position of initial contact and causing a downward force on the sample and on the planar surface in a direction normal to the planar surface; and
   f. monitoring the force detected by the force measuring means disposed below the planar surface.

10. The method according to claim 9 and further including comparing the monitored force and the preselected distance to known standards to assess the relative firmness of the sample.

11. The method according to claim 9 and including, before step (e), the step of calibrating the force measuring means to compensate for any force detected by the measuring means when such contact is made.

12. A device for testing the firmness of a substantially flat sample having opposite first and second major surfaces, the sample containing a polymeric, semi-solid, colloid or gel material, comprising:
   a) a support having a planar surface and an electrically conductive portion on the planar surface for holding the sample on its first surface, the support comprising a balance having a sensor responsive to application of force on the planar surface in a direction normal to the planar surface;
   b) a stylus to impinge on the second major surface of the sample when the stylus is displaced toward the sample;
   c) means for moving the stylus toward the sample to cause the stylus to contact the second major surface of the sample and to penetrate a predetermined distance through the second major surface into the sample; and
   d) means for detecting initial contact between the second surface of the sample and the stylus, the means comprising a first electrical contact which comprises the sample and the electrically conductive portion of the support, a second electrical contact on the stylus, and a meter between the contacts; whereby when the stylus just touches the second surface an electrical circuit is closed as indicated by the meter, and when the stylus penetrates a predetermined distance through the second major surface into the sample the support responds to the force imposed by such displacement as indicated by the balance, and the displacement and force are correlated to produce values related to the firmness, hardness, toughness or degree of cure of the material.

13. The device according to claim 12 wherein the sensor is a deflection or displacement sensor.

14. The device according to claim 12 wherein the means for moving the stylus comprises a movable shaft on which the stylus is mounted and a stationary sleeve positioned in opposed relation to the support and within which the shaft is disposed, the stationary sleeve and shaft being threadedly engaged whereby rotation of the shaft causes displacement of the stylus relative to the sleeve.

15. A method for determining the firmness of a substantially flat sample having first and second opposite major surfaces, the sample containing a polymeric, semi-solid, colloid or gel material, comprising the steps of:
   a. providing a stylus to impinge on the second major surface of the sample when the stylus is displaced toward the sample;
   b. supporting the sample on a support on its first major surface with the second major surface of the sample opposing the stylus;
   c. advancing the stylus toward the sample until initial contact is made between the tip of the stylus and the second major surface of the sample;
   d. detecting initial contact between the sample and the stylus by forming a first electrical contact which comprises the sample and an electrically conductive portion of the support, a second electrical contact on the stylus, and a meter between the contacts such that when the stylus just touches the second surface of the sample an electrical circuit is closed as indicated by the meter;
   e. moving the stylus a preselected distance into the sample from the position of initial contact and causing a force on the sample and on the support end; and
   f. monitoring the force detected by force measuring means comprising a balance having a sensor responsive to the application of force on the sample and on the support.

16. The method according to claim 15 and including, before step (e), the step of calibrating the force measuring means to compensate for any force detected by the measuring means when such contact is made.

17. The method according to claim 15 and further including comparing the monitored force and the preselected distance to known standards to assess the relative firmness of the sample.

18. The method according to claim 15 wherein the stylus is advanced toward the sample by actuating means for controlling movement of the shaft and stylus, the actuating means comprising the shaft being threadedly engaged with a stationary sleeve.

* * * * *